United States Patent
Li et al.

(10) Patent No.: US 10,464,915 B2
(45) Date of Patent: Nov. 5, 2019

(54) DAPAGLIFLOZIN CRYSTAL FORM AND PREPARATION METHOD AND USE THEREOF

(71) Applicant: Jiangsu Hansoh Pharmaceutical Group Co., Ltd., Lianyungang, Jiangsu (CN)

(72) Inventors: Xiang Li, Jiangsu (CN); Lei He, Jiangsu (CN); Jun Yu, Jiangsu (CN); Jinjia Wang, Jiangsu (CN); Zuyin Du, Jiangsu (CN)

(73) Assignee: Jiangsu Hansoh Pharmaceutical Group Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/302,332

(22) PCT Filed: May 22, 2017

(86) PCT No.: PCT/CN2017/085295
§ 371 (c)(1),
(2) Date: Nov. 16, 2018

(87) PCT Pub. No.: WO2017/202264
PCT Pub. Date: Nov. 30, 2017

(65) Prior Publication Data
US 2019/0218197 A1    Jul. 18, 2019

(30) Foreign Application Priority Data
May 24, 2016  (CN) .......................... 2016 1 0347924

(51) Int. Cl.
*C07D 309/10*  (2006.01)
*A61P 3/10*  (2006.01)

(52) U.S. Cl.
CPC .............. *C07D 309/10* (2013.01); *A61P 3/10* (2018.01); *C07B 2200/13* (2013.01)

(58) Field of Classification Search
CPC ...... C07D 309/10; A61P 3/10; C07B 2200/13
See application file for complete search history.

(56) References Cited

U.S. PATENT DOCUMENTS 9,550,747 B2 * 1/2017 Zhu .................. A61K 31/70

FOREIGN PATENT DOCUMENTS

| CN | 101479287 A | 7/2009 |
|---|---|---|
| CN | 102177147 A | 9/2011 |
| CN | 104829573 A | 8/2015 |
| WO | 2013079501 A1 | 6/2013 |
| WO | 2015117538 A1 | 8/2015 |

OTHER PUBLICATIONS

Int'l Search Report dated Aug. 25, 2017 in Int'l Application No. PCT/CN2017/085295.

* cited by examiner

*Primary Examiner* — Timothy R Rozof
(74) *Attorney, Agent, or Firm* — Panitch Schwarze Belisario & Nadel LLP

(57) ABSTRACT

Disclosed are a new dapagliflozin crystal form and a preparation method and use thereof. In particular, disclosed are a crystal form E of 2-chloro-5-(β-D-glucopyranose-1-yl)-4'-ethyoxyldiphenylmethane and a preparation method therefor, and a pharmaceutical composition containing a therapeutically effective amount of the crystal form and the use thereof in treating type II diabetes.

20 Claims, 2 Drawing Sheets

DAPAGLIFLOZIN CRYSTAL FORM AND PREPARATION METHOD AND USE THEREOF

CROSS-REFERENCE TO RELATED APPLICATION

This application is a Section 371 of International Application No. PCT/CN2017/085295, filed May 22, 2017, which was published in the Chinese language on Nov. 30, 2017, under International Publication No. WO 2017/202264 A1, which claims priority under 35 U.S.C. § 119(b) to Chinese Patent Application No. 201610347924.8, filed on May 24, 2016, the disclosures of which are incorporated herein by reference in their entireties.

FIELD OF THE INVENTION

The invention relates to the technical field of pharmaceutical crystal forms, and specifically relates to crystal form E of dapagliflozin, a preparation method and use thereof.

BACKGROUND OF THE INVENTION

Diabetes is a group of endocrine-metabolic diseases having a common marker of high blood sugar. Metabolic disorders of sugar, protein, fat and secondary water, and electrolyte are caused by absolute or relative insufficiency of insulin secretion. Diabetes can involve chronic damage and dysfunction of various systems throughout the body, especially eye, kidney, heart, blood vessel and nerves, and even induce a number of fatal complications. With the aging of the world's population, diabetes that seriously endangers human health has become a common and frequently-occurring disease. Research data shows that the number of diabetic patients worldwide has increased from 150 million in 2000 to 280 million. It is estimated that there will be nearly 500 million diabetic patients worldwide by 2030.

Glucose transporter regulates and controls the balance of glucose metabolism in the normal state of human. Sodium-glucose cotransporter (SGLT) is a known glucose transporter. SGLT includes SGLT1 and SGLT2. SGLT1 is expressed in small intestine and the distal S3 segment of renal proximal convoluted tubules, and absorbs about 10% of the sugar. SGLT2 is mainly expressed in the proximal SI segment of renal proximal convoluted tubules, and is responsible for more than 90% glucose reabsorption.

Therefore, inhibition of SGLT, particularly SGLT2, can inhibit the reabsorption of sugar, thereby allowing the sugar to be excreted in the urine and lowering the concentration of sugar in the blood.

Dapagliflozin, developed by Bristol-Myers Squibb and AstraZeneca, is used for the treatment of type II diabetes (a sodium-glucose cotransporter-2 (SGLT-2) inhibitor).

Bristol-Myers Squibb and AstraZeneca submitted an application to the European Medicines Agency (EMA) in December 2010, and the European committee for medicinal products for human use recommended the approval of dapagliflozin for the treatment of type II diabetes in April 2012.

Bristol-Myers Squibb and AstraZeneca also submitted an NDA application to the Food and Drug Administration (FDA) in December 2010. The FDA issued a response letter requesting an increase in clinical data in January 2012.

The chemical name of dapagliflozin is 2-chloro-5-(β-D-glucopyranosyl-1-yl)-4'-ethoxydiphenylmethane, and the chemical structure is as follows:

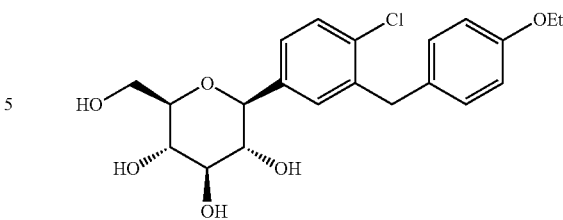

In general, for the purpose of the operability of the preparation of drug substance and formulation, the stability of the drug preservation, and improving the efficacy of the drug, it is necessary to make the drug into a crystalline state.

By far, regarding the report on crystal forms of dapagliflozin, only the original crystal form patent (CN101479287) has reported 9 crystal forms: dapagliflozin solvates and complexes of dapagliflozin and amino acids. Details are as follows:

| Crystal form | Crystal form description | Preparation method of crystal form |
|---|---|---|
| Ia | Dapagliflozin (S)-propylene glycol monohydrate | In a system of (S)-propylene glycol, water and dapagliflozin, cyclohexane and methyl tert-butyl ether were added, and the mixture was cooled to 5° C., then stirred to precipitate a crystal. |
| Ib | Dapagliflozin (R)-propylene glycol monohydrate | In a system of (R)-propylene glycol, water and dapagliflozin, cyclohexane and methyl tert-butyl ether were added, and the mixture was cooled to 5° C., then stirred to precipitate a crystal. |
| Ic | Dapagliflozin ethanol dihydrate | Dapagliflozin was dissolved in ethanol, and the mixture was diluted with water and cooled to −10 to −20° C., and then stirred to precipitate a crystal. |
| Id | Dapagliflozin ethylene glycol dihydrate | Dapagliflozin was dissolved in ethylene glycol aqueous solution, and crystal Ia was added, and then stirred to precipitate a crystal. |
| Ie | Dapagliflozin ethylene glycol dihydrate | Dapagliflozin was dissolved in ethylene glycol aqueous solution, and crystal Ic was added, and then stirred to precipitate a crystal. |
| Ih | Dapagliflozin-di-L-proline complex | L-proline was dissolved in water under heating. Isopropanol and a solution of dapagliflozin in isopropanol were added successively to precipitate a crystal. |
| Ii | Dapagliflozin-L-proline complex | L-proline was dissolved in 90% ethanol/water under heating. A solution of dapagliflozin in ethanol was added, and then the mixture was cooled to −20° C. to precipitate a crystal. |
| Ij | Dapagliflozin-L-proline semihydrate | L-proline and dapagliflozin were dissolved in 97% ethanol/water under heating. The mixture was cooled to −20° C. before adding crystal Ii, and then stirred to obtain a white solid Ij in the form of a complex. |
| Ik | Dapagliflozin-L-phenylalanine complex | L-phenylalanine was dissolved in water under heating, and then added to a solution of dapagliflozin in ethanol to obtain the complex Ik. |

It is well known that, when a drug crystal exists in the form of a solvate or a complex, in addition to the active ingredient (i.e., API) having a therapeutic effect in the drug substances, there are some substances which are not related to the therapeutic effect of the drug, and are often harmful to the human body. In the formula study of formulations, as for a drug in the form of solvates or complexes, due to the presence of non-API components, the compatibility of drug substances and auxiliary materials, the ratio of drug substances and auxiliary materials, and the weight of the formulations are often affected. Therefore, the drug crystal form which is generally present in the form of a solvate or a complex is not suitable for the development of pharmaceutical preparations.

In addition, the patent application WO2013079501A disclosed crystal forms A and B of dapagliflozin hydrate. WO2015117538A and CN104829573A disclosed a new crystal form of dapagliflozin, respectively. These crystal forms disclosed in the above patent applications are not crystal forms of solvates. However, it is found that the melting points of the above crystal forms are too low, less than 35° C. by the DSC melting point test. During the tableting process, the local temperature was too high, thereby causing the active material to melt, which is not conducive to drug production.

SUMMARY OF THE INVENTION

An objective of the present invention is to provide a new crystal form E of dapagliflozin.

Another objective of the present invention is to provide a method for preparing the crystal form E of dapagliflozin.

Still another objective of the present invention is to provide a pharmaceutical composition comprising the crystal form E of dapagliflozin as an active ingredient, and one or more pharmaceutically acceptable excipients, and the use thereof as a SGLT-2 inhibitor.

The objectives of the present invention are achieved by the following technical solutions:

The present invention provides a crystal form E of dapagliflozin, wherein its X-ray powder diffraction (XRPD) spectrum comprises characteristic peaks at 2θ of 3.5±0.2, 4.1±0.2, 5.1±0.2, 7.3±0.2, 14.0±0.2, and 14.8±0.2, 19.1±0.2, and 21.8±0.2.

Preferably, the present invention provides the crystal form E of dapagliflozin, wherein its X-ray powder diffraction spectrum comprises characteristic peaks at 2θ of 3.5±0.2, 4.1±0.2, 5.1±0.2, 6.6±0.2, 7.3±0.2. 8.0±0.2, 9.0±0.2, 9.4±0.2, 10.3±0.2, 10.9±0.2, 13.0±0.2, 14.0±0.2, 14.8±0.2, 15.7±0.2, 16.5±0.2, 18.2±0.2, 19.1±0.2, 21.0±0.2, and 21.8±0.2.

Further preferably, in a typical embodiment, the XRPD spectrum of the crystal form E of dapagliflozin according to the present invention is as shown in FIG. 1.

The invention also provides a preparation method for the crystal form E of dapagliflozin, comprising the following steps of:

(1) placing dapagliflozin in an ester solvent or a mixed solvent of an ester and other solvent to form a solution;

(2) saturating the solution by cooling or addition of a poor solvent or by both cooling and addition of a poor solvent;

(3) adding a seed crystal, stirring the solution to precipitate a solid and filtering the solid; and (4) converting the resulting solid to crystal form E by solvent removal, wherein, the mass-to-volume ratio of dapagliflozin to the ester solvent in step (1) is 1:2~10, preferably 1:2.5~10, and more preferably 1:4~5.

The ester solvent in step (1) is generally an ester solvent having 2 to 6 carbon atoms, preferably an ester solvent having 3 to 5 carbon atoms, and more preferably ethyl formate, ethyl acetate or n-propyl acetate.

The mass-to-volume ratio of dapagliflozin to the poor solvent in step 2) is 1:20~70, preferably 1:22.5~50, and more preferably 1:30~40.

The poor solvent in step 2) is a liquid alkane solvent or an ether solvent, preferably a liquid alkane solvent, and more preferably n-hexane, n-heptane or n-octane.

The cooling in step (2) means that the temperature of the solution is lowered to below 0° C., preferably 0° C. to −20° C.

The seed crystal in step (3) can be prepared by the following method, specifically comprising: adding dapagliflozin to a reactor, adding an ester solvent to dissolve dapagliflozin completely at room temperature, cooling, standing, and precipitating to a solid, then adding n-heptane as an anti-solvent, stirring the mixture, and filtering it to obtain a solid that can be used as a seed crystal. The ester solvent is generally an ester solvent having 2~6 carbon atoms, preferably an ester solvent having 3~5 carbon atoms, and more preferably ethyl formate, ethyl acetate and n-propyl acetate.

Preferably, the seed crystal in step (3) is prepared by the following method, specifically comprising: adding dapagliflozin to a reactor, adding an ester solvent having a volume of twice the mass of dapagliflozin to dissolve dapagliflozin completely at room temperature, then cooling to −20° C., standing for 2 days to precipitate a solid, adding n-heptane having a volume of 5 times the mass of dapagliflozin, stirring the mixture for 24 hours, and filtering it to obtain a solid that can be used as a seed crystal.

The solvent removal in step (4) is carried out under vacuum and heating conditions. The inventors have found that vacuum and heating can speed up the solvent removal to achieve industrial production, especially in the condition of heating, the rate of solvent removal is very remarkable.

Further, the temperature of solvent removal is generally 25° C.-80° C., preferably 40° C.-70° C., and more preferably 50° C.-60° C.

Further, the time of solvent removal is generally 1 hour to 48 hours, preferably 20 hours to 24 hours.

The present invention also provides a pharmaceutical composition comprising the crystal form E of dapagliflozin as an active ingredient and one or more pharmaceutically acceptable excipients. The pharmaceutical composition can be applied to mammals, including humans, baboons, and dogs, and administered in the form of tablets, capsules, granules, injections, intranasal administration or dermal patches as well.

The crystal form E of dapagliflozin according to the present invention may be used alone or in combination with one or more other anti-diabetic agents, anti-hyperglycemic agents, or agents for treating other diseases. When the crystal form E of dapagliflozin according to the present invention is used with other therapeutic agents, it can be administered in the same dosage form or in separate oral dosage forms or injections.

Compared to the prior art, the beneficial effects of the present invention are as follows:

1) The crystal form E of dapagliflozin is a crystal form of a solvent-free compound, that is, there is no other solvent molecules in the crystal lattice except for the drug molecule, which makes the drug crystal form safer and more pure, improves the safety of drug use, and obtains a more obvious effect on the therapeutic effect of diabetes. Moreover, the melting point of the crystal form E reaches 70° C., which can meet the medicinal requirements, compared to the existing crystal forms of non-solvate compounds.

2) The crystal form E of dapagliflozin has good high temperature stability and light stability, which is conducive to the processing, transportation and storage of drugs.

3) The crystal form E of dapagliflozin has a small solid particle size, a narrower particle size distribution range, and better fluidity, which is conducive to the dug processing, and avoids the occurrence of serious aggregation and clumping.

DETAILED DESCRIPTION OF THE INVENTION

Figure 1:
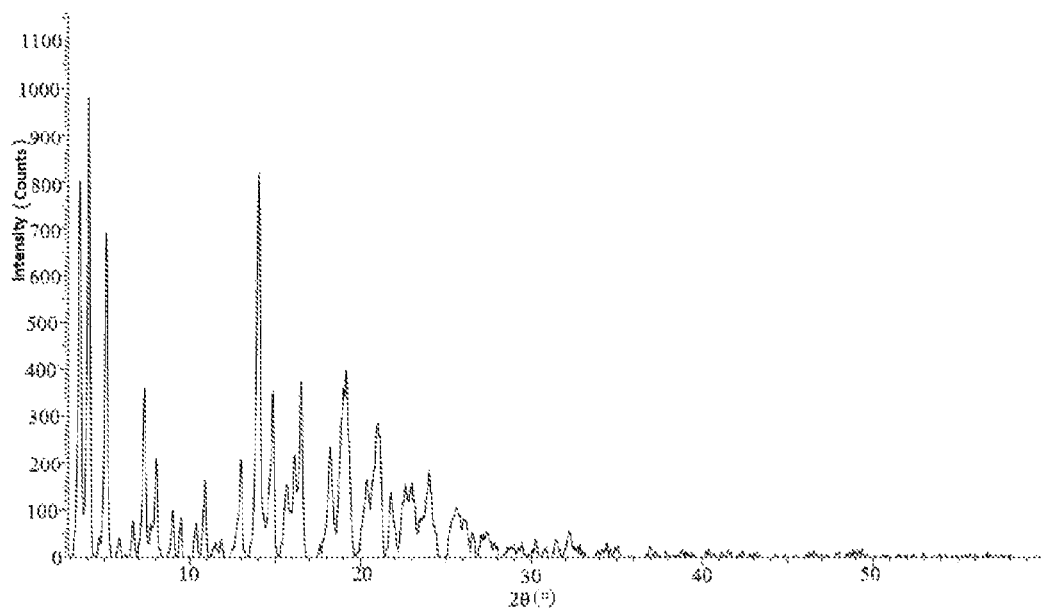
FIG. 1 shows the X-ray powder diffraction spectrum of crystal form E of dapagliflozin.
Figure 2:
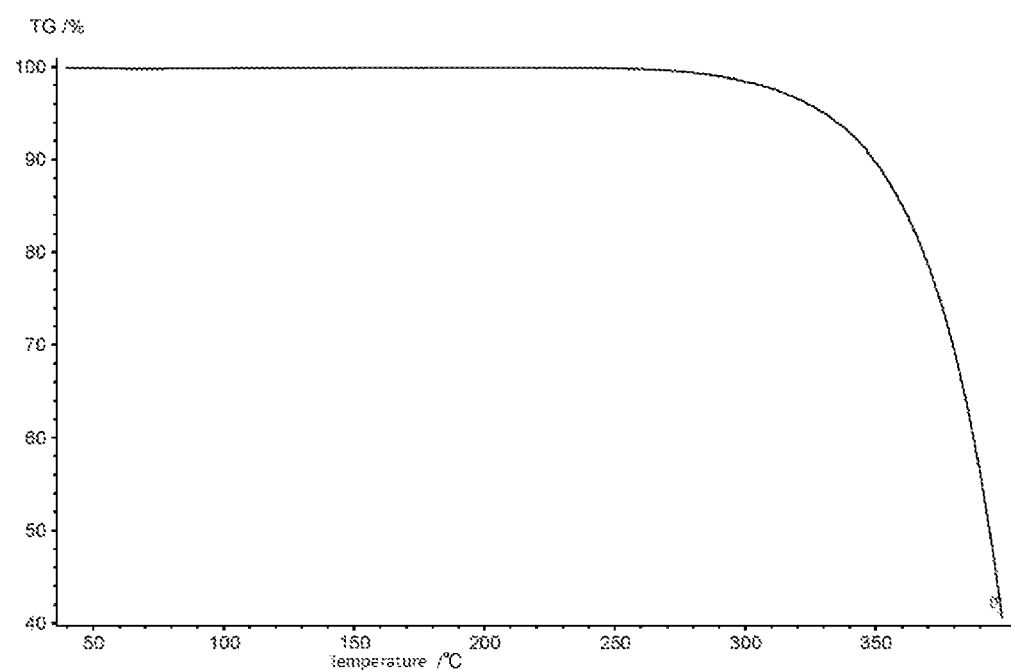
FIG. 2 shows the Thermogravimetric Analysis (TGA) spectrum of crystal form E of dapagliflozin.
Figure 3:
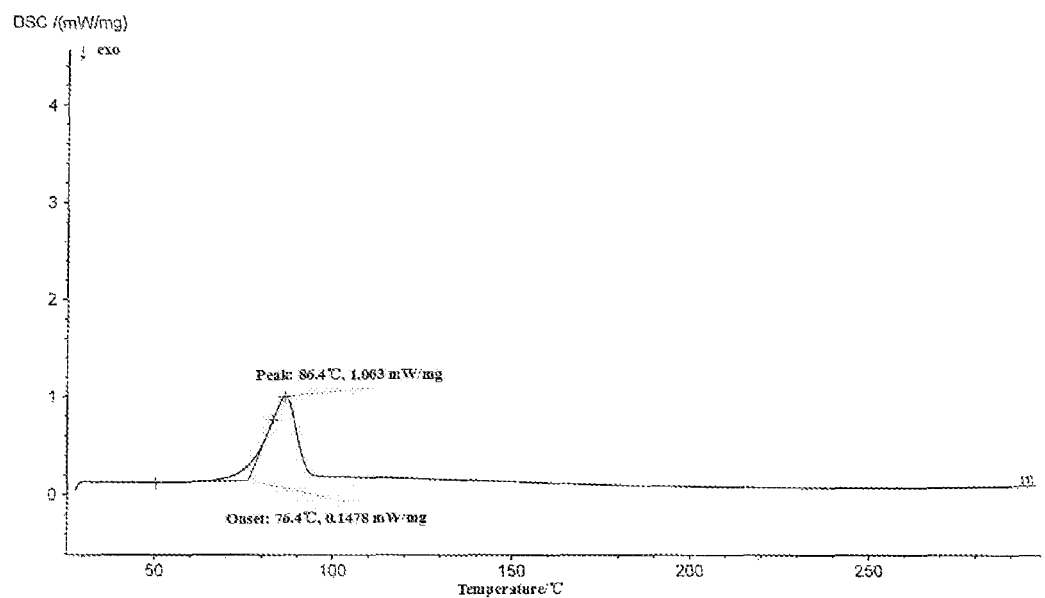
FIG. 3 shows the Differential Scanning Calorimetry (DSC) spectrum of crystal form E of dapagliflozin.

The specific embodiments according to the present invention are further described in detail below with reference to the drawings and examples. The following examples are intended to illustrate the present invention, but are not intended to limit the scope of the invention.

Example 1: Preparation of Seed Crystal 1 g of dapagliflozin was weighed and added into a reactor, and then 2.0 mL of ethyl acetate was added at room temperature to dissolve the sample completely. Then, the mixture was cooled to −20° C., left to stand for 2 days, and a solid was precipitated. 5 mL of n-heptane was added into the above reactor, and the mixture was stirred for 24 hours. The suspension was filtered to obtain a solid containing ethyl acetate, which was used as a seed crystal.

Example 2: Preparation of Seed Crystal

According to a method similar to that of Example 1, ethyl acetate was replaced with ethyl formate to prepare a seed crystal containing ethyl formate.

Example 3: Preparation of Seed Crystal

According to a method similar to that of Example 1, ethyl acetate was replaced with isopropyl acetate to prepare a seed crystal containing isopropyl acetate.

Example 4

10 g of dapagliflozin was weighed and added into a reactor, 25.0 mL of ethyl acetate was added at room temperature to dissolve the sample completely, and then 25.0 mL of n-heptane was added into the reactor. The system became turbid, and the seed crystal obtained in Example 1 was added. After stirring for 4 hours, the mixture was added with 200 mL of n-heptane, and stirred for 24 hours. The suspension was filtered to obtain a solid, which was dried under vacuum at 50° C. for 24 hours, and then a solid crystal form E was obtained.

Example 5

500 g of dapagliflozin was weighed and added into a reactor, 2.0 L of ethyl acetate was added at room temperature to dissolve the sample completely, and then 2.3 L of n-heptane was added into the reactor. The system became turbid, and the seed crystal obtained in Example 1 was added. After stirring for 4 hours, the mixture was added with 12.7 L of n-heptane, and stirred for 24 hours. The suspension was filtered to obtain a solid, which was dried under vacuum at 60° C. for 24 hours, and then a solid crystal form E was obtained.

Example 6

25 g of dapagliflozin was weighed and added into a reactor, 100.0 mL of ethyl formate was added at room temperature to dissolve the sample completely, and then 100.0 mL of n-heptane was added into the reactor. The system became turbid, and the seed crystal obtained in Example 2 was added. After stirring for 4 hours, the mixture was added with 1.5 L of n-heptane and stirred for 24 hours. The suspension was filtered to obtain a solid, which was dried under vacuum at 50° C. for 24 hours, and then a solid crystal form E was obtained.

Example 7

10 g of dapagliflozin was weighed and added into a reactor, 40.0 mL of isopropyl acetate was added at room temperature to dissolve the sample completely, and then 40.0 mL of n-heptane was added into the reactor. The system became turbid, and the seed crystal obtained in Example 3 was added. After stirring for 4 hours, the mixture was added with 460 mL of n-heptane, and stirred for 24 hours. The suspension was filtered to obtain a solid, which was dried under vacuum at 60° C. for 24 hours, and then a solid crystal form E was obtained.

Example 8

20 g of dapagliflozin was weighed and added into a reactor, 50.0 mL of n-propyl acetate was added at room temperature to dissolve the sample completely, and then 50.0 mL of n-heptane was added into the reactor. The system became turbid, and the seed crystal obtained in Example 3 was added. After stirring for 5 hours, the mixture was added with 750 mL of n-heptane, and stirred for 24 hours. The suspension was filtered to obtain a solid, which was dried under vacuum at 60° C. for 12 hours, and then a solid of crystal form E was obtained.

Example 9

20 g of dapagliflozin was weighed and added into a reactor, 50.0 mL of n-propyl acetate was added at room temperature to dissolve the sample completely, and then 50.0 mL of n-heptane was added into the reactor. The system became turbid, and the seed crystal obtained in Example 3 was added. After stirring for 5 hours, the mixture was added with 750 mL of n-heptane, and stirred for 24 hours. The suspension was filtered to obtain a solid, which was dried under vacuum at 30° C. for 48 hours. After comparing XPRD, it was found that only a small amount of solvate was converted into crystal form E.

Example 10: Preparation of Seed Crystal

According to a method similar to that of Example 1, ethyl acetate was replaced with ethanol to prepare a seed crystal containing ethanol.

Example 11

20 g of dapagliflozin was weighed and added into a reactor, 50.0 mL of ethanol was added at room temperature to dissolve the sample completely, and then 50.0 mL of n-heptane was added into the reactor. The system became turbid, and the seed crystal obtained in Example 10 was added. After stirring for 5 hours, the mixture was added with 750 mL of n-heptane, and stirred for 24 hours. The suspension was filtered to obtain a solid, which was dried under vacuum at 60° C. for 24 hours. After comparing XPRD, it was found that crystal form E was not prepared.

Example 12: Stability Study of Crystal Form E

In the course of the study, the influencing factors tests and accelerated tests were carried out on the samples of crystal form E of dapagliflozin. The experimental contents and results are shown as follows:

(1) Contents and results of influencing factors tests

| Test conditions | Time | Crystal form | Purity |
|---|---|---|---|
| Lighting (5000 lux) | 0 day | Crystal form E | 99.9% |
| | 5 days | Crystal form E | 99.9% |
| | 10 days | Crystal form E | 99.9% |
| | 30 days | Crystal form E | 99.9% |
| 40° C. | 0 day | Crystal form E | 99.9% |
| | 5 days | Crystal form E | 99.9% |
| | 10 days | Crystal form E | 99.9% |
| | 30 days | Crystal form E | 99.9% |

The experimental results showed that the samples of crystal form E of dapagliflozin were stable for at least 30 days under high temperature (40° C.) and lighting (5000 Lux).

(2) Contents and results of accelerated tests

| Test conditions | Time | Crystal form | Purity |
|---|---|---|---|
| 25° C. | 0 day | Crystal form E | 99.9% |
| | 1 month | Crystal form E | 99.9% |
| | 3 months | Crystal form E | 99.9% |
| | 6 months | Crystal form E | 99.9% |

The experimental results showed that the samples of crystal form E of dapagliflozin were stable for at least 6 months at a condition of 25° C.

The results of influencing factors tests and accelerated tests showed that the stability of crystal form E of dapagliflozin could meet the medicinal requirements.

Example 13: Tableting Test

Figure 4:
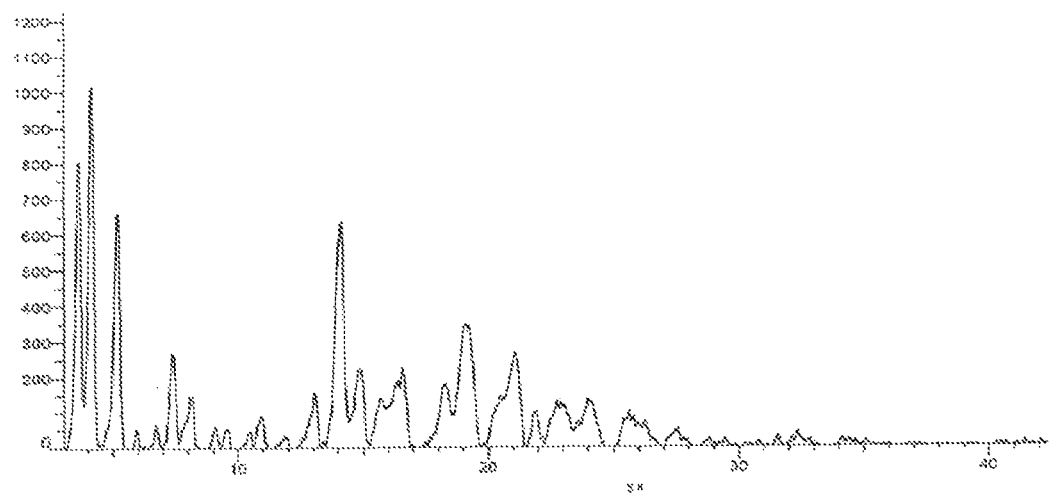
FIG. 4 shows the X-ray powder diffraction spectrum of crystal form E of dapagliflozin after being compressed into tablets.

The crystal form prepared in the Example 8 of the present invention was directly compressed by a tableting machine, and the control pressure was 10 KN. It can be seen from FIG. 4 that the crystal form E of the present invention didn't undergo crystal form transformation, indicating that the crystal form according to the present invention was stable under the tableting conditions.

Example 14: Preparation of Dapagliflozin Tablets

Dapagliflozin tablets were prepared according to the following formula:

| Components | g/1000 tablets |
|---|---|
| Crystal form E of dapagliflozin | 10 |
| Microcrystalline cellulose | 105 |
| Lactose | 100 |
| Crospovidone | 25 |
| Silicon dioxide | 5 |
| Magnesium stearate | 5 |
| Film coating premix (stomach soluble) | 5~10 |

Preparation process: Crystal form E of dapagliflozin, microcrystalline cellulose, lactose, and crospovidone were added into a mixer, rotated at 10 rpm, and mixed for 30 min. Granules were prepared by a dry granulator. Then, silicon dioxide and magnesium stearate were added into the mixer, rotated at 10 rpm, and mixed for 5 min. The mixed materials were compressed into tablets by a rotary tableting machine. The compressed raw tablets were coated by a high-efficiency coating machine, and the temperature of tablet bed was 40~45° C. The results of specific process steps are shown as follows:

| Process | Results |
|---|---|
| mixing | Content RSD <3% at five different sampling points, good mixing uniformity |
| Total mixing | Content RSD <3% at five different sampling points, good mixing uniformity |
| Tableting | The tableting speed was 50,000 tablets/hour, the tableting was carried out smoothly, the surface of the resulting tablets was smooth and complete, and there was no sticking phenomenon. The hardness was 6~7 kg/cm² at the beginning, middle and end of tableting. According to the method of the New Chinese Pharmacopoeia, the content uniformity was detected, A + 2.2S ≤ 5. |
| Coating | The coating efficiency was high, and the target weight gain could be achieved in a short time. The surface of the resulting tablets was smooth, uniformly colored, without spots or pitting. |

The dapagliflozin tablets prepared by tableting was determined by XPRD, and the characteristic peaks were consistent through spectrum comparison, indicating that the crystal form E does not undergo crystal form transformation. Under the conditions of 40° C. and 60% relative humidity, the crystal form remained consistent, and no crystal transformation occurred after 3 months or 6 months of long-term placement.

The above examples are only preferred embodiments according to the present invention. It should be noted that, without departing from the technical principles of the present invention, a person skilled in the art can make some improvements and modifications, which should also be considered as the protection scope of the present invention.

What is claimed is:

1. Crystal form E of dapagliflozin, wherein the crystal form E is characterized by an X-ray powder diffraction spectrum comprising diffraction peaks at angles 2θ of 3.5±0.2, 4.1±0.2, 5.1±0.2, 7.3±0.2, 14.0±0.2, and 14.8±0.2, 19.1±0.2, and 21.8±0.2.

2. The crystal form E of dapagliflozin according to claim 1, wherein the X-ray powder diffraction spectrum comprises diffraction peaks at angles 2θ of 3.5±0.2, 4.1±0.2, 5.1±0.2, 6.6±0.2, 7.3±0.2, 8.0±0.2, 9.0±0.2, 9.4±0.2, 10.3±0.2, 10.9±0.2, 13.0±0.2, 14.0±0.2, 14.8±0.2, 15.7±0.2, 16.5±0.2, 18.2±0.2, 19.1±0.2, 21.0±0.2, and 21.8±0.2.

3. The crystal form E of dapagliflozin according to claim 1, wherein the X-ray powder diffraction spectrum is substantially as shown in FIG. 1.

4. A preparation method for crystal form E of dapagliflozin, comprising:
1)(a) placing dapagliflozin in an ester solvent or a mixed solvent of an ester solvent and other solvent to form a solution;
2) saturating the solution by cooling or addition of a poor solvent or by both cooling and addition of a poor solvent;
3)(c) adding a seed crystal, stirring the solution to precipitate a solid and filtering the solid; and
4)(d) converting the solid to crystal form E by solvent removal.

5. The preparation method according to claim 4, wherein a mass-to-volume ratio of dapagliflozin to the ester solvent in step (a) is 1:2 to 10.

6. The preparation method according to claim 4, wherein the ester solvent in step (a) is an ester solvent having 2 to 6 carbon atoms.

7. The preparation method according to claim 4, wherein a mass-to-volume ratio of dapagliflozin to the poor solvent in step (b) is 1:20 to 70.

8. The preparation method according to claim 4, wherein the poor solvent in step (b) is a liquid alkane solvent or an ether solvent.

9. The preparation method according to claim 4, wherein the solvent removal in step (d) is carried out under vacuum and heating conditions.

10. The preparation method according to claim 4, wherein the solvent removal in step (d) is carried out at a temperature of 25° C. to 80° C.

11. A pharmaceutical composition comprising an effective amount of the crystal form E of dapagliflozin according to claim 1 and one or more pharmaceutically acceptable excipients.

12. A method for treating type II diabetes I in a subject, comprising administering to the subject a therapeutically effective amount of the pharmaceutical composition according to claim 11.

13. The preparation method according to claim 5, wherein the mass-to-volume ratio of dapagliflozin to the ester solvent in step (a) is 1:2.5 to 10.

14. The preparation method according to claim 5, wherein the mass-to-volume ratio of dapagliflozin to the ester solvent in step (a) is 1:4 to 5.

15. The preparation method according to claim 6, wherein the ester solvent has 3 to 5 carbon atoms.

16. The preparation method according to claim 6, wherein the ester solvent is ethyl formate, ethyl acetate or n-propyl acetate.

17. The preparation method according to claim 7, wherein the mass-to-volume ratio of dapagliflozin to the poor solvent in step (b) is 1:30 to 40.

18. The preparation method according to claim 8, wherein the poor solvent is a liquid alkane solvent.

19. The preparation method according to claim 18, wherein the liquid alkane solvent is n-hexane, n-heptane or n-octane.

20. The preparation method according to claim 4, wherein the solvent removal in step (d) is carried out at a temperature of 50° C. to 60° C.

* * * * *